(12) United States Patent
Lang

(10) Patent No.: US 7,890,160 B2
(45) Date of Patent: Feb. 15, 2011

(54) HEART MONITORING SYSTEM

(75) Inventor: Volker Lang, West Linn, OR (US)

(73) Assignee: Biotronik CRM Patent AG, Baar (CH)

( * ) Notice: Subject to any disclaimer, the term of this patent is extended or adjusted under 35 U.S.C. 154(b) by 838 days.

(21) Appl. No.: 11/847,603

(22) Filed: Aug. 30, 2007

(65) Prior Publication Data

US 2009/0062878 A1    Mar. 5, 2009

(51) Int. Cl.
*A61B 5/04*    (2006.01)
(52) U.S. Cl. .......................... 600/513; 600/508; 600/526
(58) Field of Classification Search .................. 600/508, 600/513, 526; 607/32, 30, 24
See application file for complete search history.

(56) References Cited

U.S. PATENT DOCUMENTS

| | | | |
|---|---|---|---|
| 6,512,949 B1 | 1/2003 | Combs et al. | |
| 2004/0186526 A1* | 9/2004 | Freeberg | 607/17 |
| 2006/0010090 A1* | 1/2006 | Brockway et al. | 706/46 |

FOREIGN PATENT DOCUMENTS

| | | |
|---|---|---|
| WO | WO 98/33554 | 8/1998 |
| WO | WO 2007/035696 | 3/2007 |
| WO | WO 2007/092212 | 8/2007 |

OTHER PUBLICATIONS

European Search Report, dated May 12, 2008.
\* cited by examiner

*Primary Examiner*—Carl H Layno
*Assistant Examiner*—Natasha N Patel
(74) *Attorney, Agent, or Firm*—ARC IP Law, PC; Joseph J. Mayo

(57) ABSTRACT

Heart monitoring system includes implantable medical device and service center. Implantable medical device includes stimulation pulse generator, ventricular sensing stage, activity sensor, impedance determination unit with a constant current or voltage source to generate sub-threshold measuring current pulses having constant current strength or constant voltage, measuring unit for measuring a voltage corresponding to a current fed through a body, impedance value determination unit connected with measuring unit adapted to determine impedance value for each measuring current pulse, and perform intrathoracic impedance measurement, a control unit adapted to collect data representing values of changes, and initiate data transmission, implant transceiver unit communicating with the service center with a data evaluation module including data trending of stored data with a user interface and said data evaluation module adapted to allow a physician to set for each data trend trigger criteria for decompensation detection and generate a decompensation indicator signal.

14 Claims, 4 Drawing Sheets

HEART MONITORING SYSTEM

BACKGROUND OF THE INVENTION

1. Field of the Invention

The invention relates to a heart monitoring system comprising an implantable medical device, an external transceiver device and a service center. The implantable medical device preferably is an implantable pacemaker or an implantable cardioverter/defibrillator (ICD) or a combination of both (CRT-D).

2. Description of the Related Art

Some patients having an implantable pacemaker or an implantable cardioverter/defibrillator eventually suffer from decompensation. Decompensation needs to be detected and to be treated.

The detection of decompensation of CRT patients with lung edema sensor (detection of offset of the DC-impedance versus baseline) lacks of specificity (personal reports from many physicians). Several patents exists which describes that combination of additional parameters (HRV, breathing, HR) with the DC impedance offset may increase specificity.

If decompensation in CRT patients are detected (e.g. with lung edema sensor (DC offset via impedance) or combination of additional parameters (HRV, breathing, HR), then the physician needs to react and change CRT therapy.

U.S. Pat. No. 6,512,949 discloses a device that changes CRT therapy or activates drug pump automatically. This keeps the physician out of the loop for feedback and therapy control.

BRIEF SUMMARY OF THE INVENTION

It is an object of the invention to provide a heart monitoring system that allows an improved detection of and response to decompensation.

According to one aspect of the invention it is proposed to use central service center as integral part of the problem solving. Instead of fixed threshold values/algorithms in the device the data of several indicators for CHF status are sent to the service center preferably once a day. The parameters that serve as indicators and that are to be transferred and monitored include:

(1) DC thoracic impedance from lead combination 1 and its changes.

(2) DC thoracic impedance from lead combination 2 and its changes.

(3) heart rate variability and its changes (4) heart rate at rest (5) heart rate during exercise.

(6) activity level (7) VES per h (8) breathing rate (9) tidal volume

(10) weight

(11) (12) parameters from at least another sensor (contractility of the heart, pressure, temperature)

(13) diet

The service center stores the data. Furthermore, the service center provides trends of the data in one graph or more graphs to allow visual inspection of the trends, changes of trends, and the timely coincidence of changes in the trends. A user interface being connected to the service center or being part of the service center is adapted to allow the physician to set for each trend its own, patients customized trigger criteria. The trigger criteria may include offset versus baseline or slope (positive and negative) or others.

Preferably, the user interface is adapted so that the physician can set trigger combination and its timely coincidence to receive alarm (via e-mail or otherwise); e.g. only by increase of both impedance vectors by x % and decrease of activity level by y % and increase of breathing rate by z % the service center triggers a decompensation alarm: "alarm—potential decompensation".

The service center and the user interface are adapted to interact such that the user receives a set of standard triggers/trigger combination by the service center that is stored in the service center the user can store its own trigger logic and apply it to other patients a supervisor can collect the data of trigger logic from all patients and all users (physicians) and generated there from an improved set standard trigger criteria Alternatively the following features may be provided:

Additional data is collected from outside sensors

Weight is determined via a scale which sends weight data to the service center blood pressure data is collected via manual or automatic measurements and the results are send to the service center Diet information data is determined via barcode in a refrigerator and is send to the service center Duration of daily exercise (treadmill reports duration/speed/activity level) are transmitted to the service center Preferably the collected data is transmitted daily to the service center to allow trends with the same time basis.

The data evaluation module preferably is adapted to trend the data with one datapoint per day for each trend.

Regarding embodiments of the data evaluation module and the user interface and their interaction it is further preferred that they are adapted to allow a user to be able to activate/deactivate trigger for each trend (absolute value, positive/negative slope, duration of increase, 30 day line (to compensate for biological variations), 7 day line)

a user to be able to combine trigger to trigger logic comprising a combination of trigger criteria to be met definition of a timely coincidence of triggers ("within 2 days")

a display of data wherein graph-lines changes colors for each trend separately if trigger is not reached ("green") versus trigger is reached ("red")

a display of data wherein a graph background changes colors for times for which the trigger logic was giving alarm ("alarm background")

Another aspect of the invention is concerned with a response to a decompensation once detected. According to this aspect of the invention the service center is adapted to indicate a decompensation via a user interface connected to the service center and to allow the physician to initiate therapy changes actively via several remote activities including:

Change of CRT parameters (e.g. % LV pacing was seen to be insufficient, then AVD would be adapted) via remote programming via the user interface Change of diet via telephone call to the patients Change of medication (Lasix) via telephone call to the patients Change of medication (Lasix) via remote programming of a drug pump using the user interface of the service center.

Further, a feedback channel from an individual patient to the physician may be provided that allows for a feedback whether a therapy change was successful or not.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
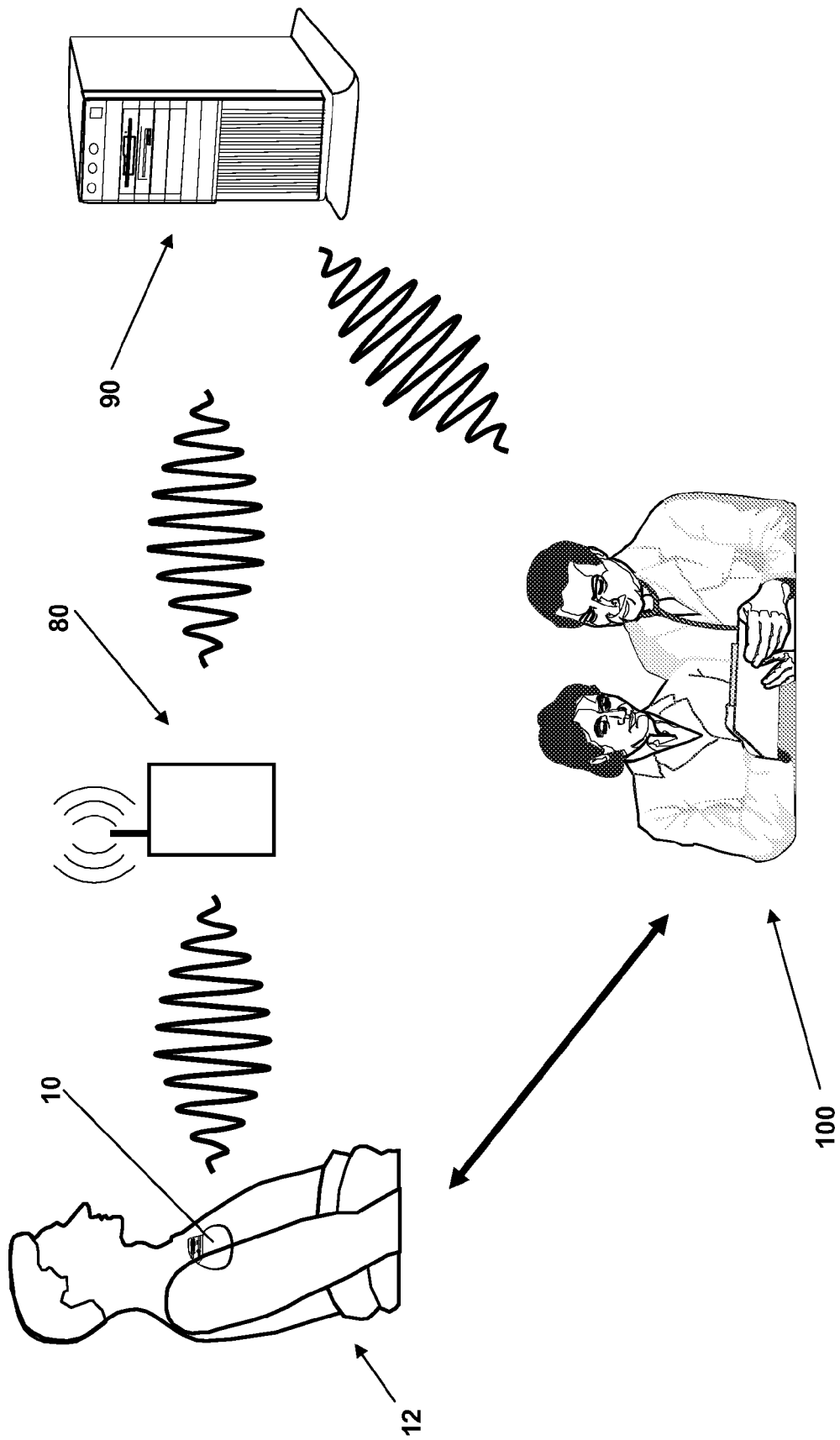
FIG. 1 is a schematic overview over a heart monitoring system comprising an implantable medical device, an external transceiver device and a service center.

FIG. 1 shows an implantable device system comprising an implantable medical device 10, an external transceiver device 80 and a central service center 90. The implantable medical device 10 is for example an implantable pacemaker or an implantable cardioverter/defibrillator or a combination of both. The implantable medical device 10 comprises an implant transceiver for wireless communication with the external transceiver device 80. The external transceiver device 80 comprises an external transceiver unit (not shown) for wireless communication with the implant transceiver unit and a data communication interface (also not shown) adapted to allow a data communication with the service center 90. The data communication interface preferably is adapted to use a public data communication line as a telephone landline connection or wireless connection via GPRS or SMS or Bluetooth.

The central service center 90 comprises or is connected to a user interface allowing a physician or a team of physicians to interact with the central service center. The user interface may comprise a display for displaying data to the physician 100 and some input device allowing the physician 100 to enter instructions or data into the central service center 90. The central service center 90 further comprises a central data base that is connected to said data communication interface (see FIG. 4) and a data evaluation module that is connected to the data base that is adapted to evaluate data stored and said data base.

Figure 2:
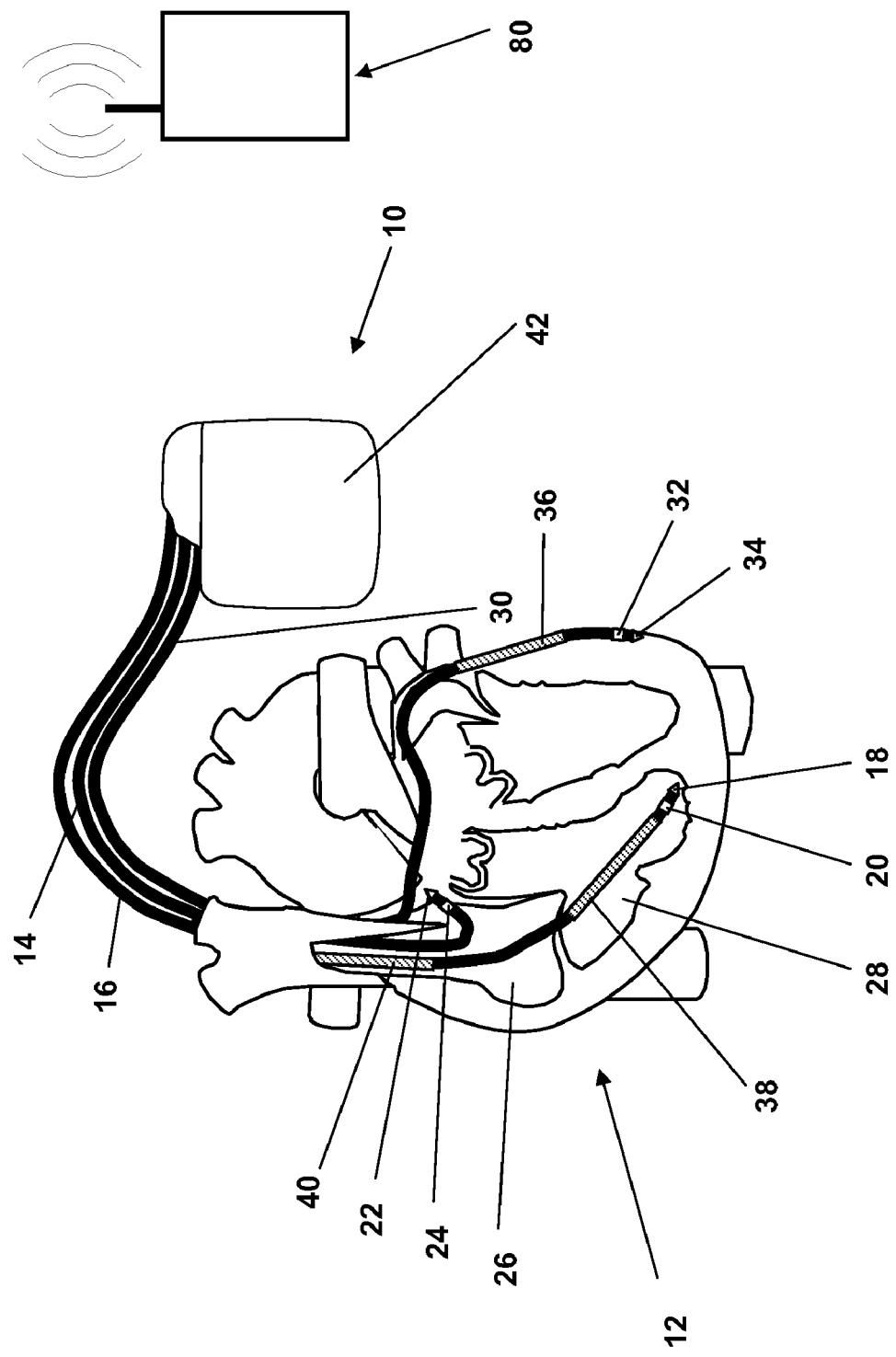
FIG. 2 shows a three chamber bi-ventricular implantable cardioverter/defibrillator (ICD).

In FIG. 2 the implantable medical device is a three chamber biventricular pacemaker and cardioverter/defibrillator 10 that is connected to pacing/sensing leads placed in a heart 12 is illustrated.

As shown in FIG. 2, the preferred embodiment is to couple the disclosed technology with an implantable bi-ventricular defibrillator.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32 a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

The forcing function for intrathoracic impedance measurement preferably is sourced via the right ventricular or a left ventricular ring electrode and the current sink would be the implantable medical device's case. Measurement of the response function preferably is carried out between a right ventricular tip electrode and the implantable medical device's case or a left ventricular tip electrode and the implantable medical device's case.

For intracardiac impedance measurements, injecting a forcing function from a right ventricular ring electrode to a right ventricular tip electrode and measuring a response function between a left ventricular ring electrode and a left ventricular tip electrode is preferred.

Further possible electrode configurations for application of the forcing function and measurement of the response function become apparent from the following table:

| Diagnostic Value | Polarity | Forcing contacts | Response contacts |
| --- | --- | --- | --- |
| Primary | Tripolar | RV Ring to Case | RV Tip to Case |
| Primary | Tripolar | LV Ring to Case | LV Tip to Case |
| Primary | Bipolar | RV Coil to Case | RV Coil to Case |
| Primary | Bipolar | LV Coil to Case | LV Coil to Case |
| Secondary | Quadrapolar #1 | LV Ring to RV Ring | LV Tip to RV Tip |
| Secondary | Quadrapolar #2 | RV Ring to RV Tip | LV Ring to LV Tip |
| Secondary | Tripolar | RV Ring to LV Ring | RV Tip to LV Ring |
| Secondary | Tripolar | RV Ring to LV Tip | RV Tip to LV Tip |
| Secondary | Tripolar | LV Ring to RV Ring | LV Tip to RV Ring |
| Secondary | Tripolar | LV Ring to RV Tip | LV Tip to RV Tip |
| Secondary | Bipolar | RV Ring to LV Ring | RV Ring to LV Ring |
| Secondary | Bipolar | RV Tip to LV Tip | RV Tip to LV Tip |

-continued

| Diagnostic Value | Polarity | Forcing contacts | Response contacts |
|---|---|---|---|
| Secondary | Bipolar | RV Ring to LV Tip | RV Ring to LV Tip |
| Secondary | Bipolar | RV Tip to LV Ring | RV Tip to LV Ring |

Figure 3:
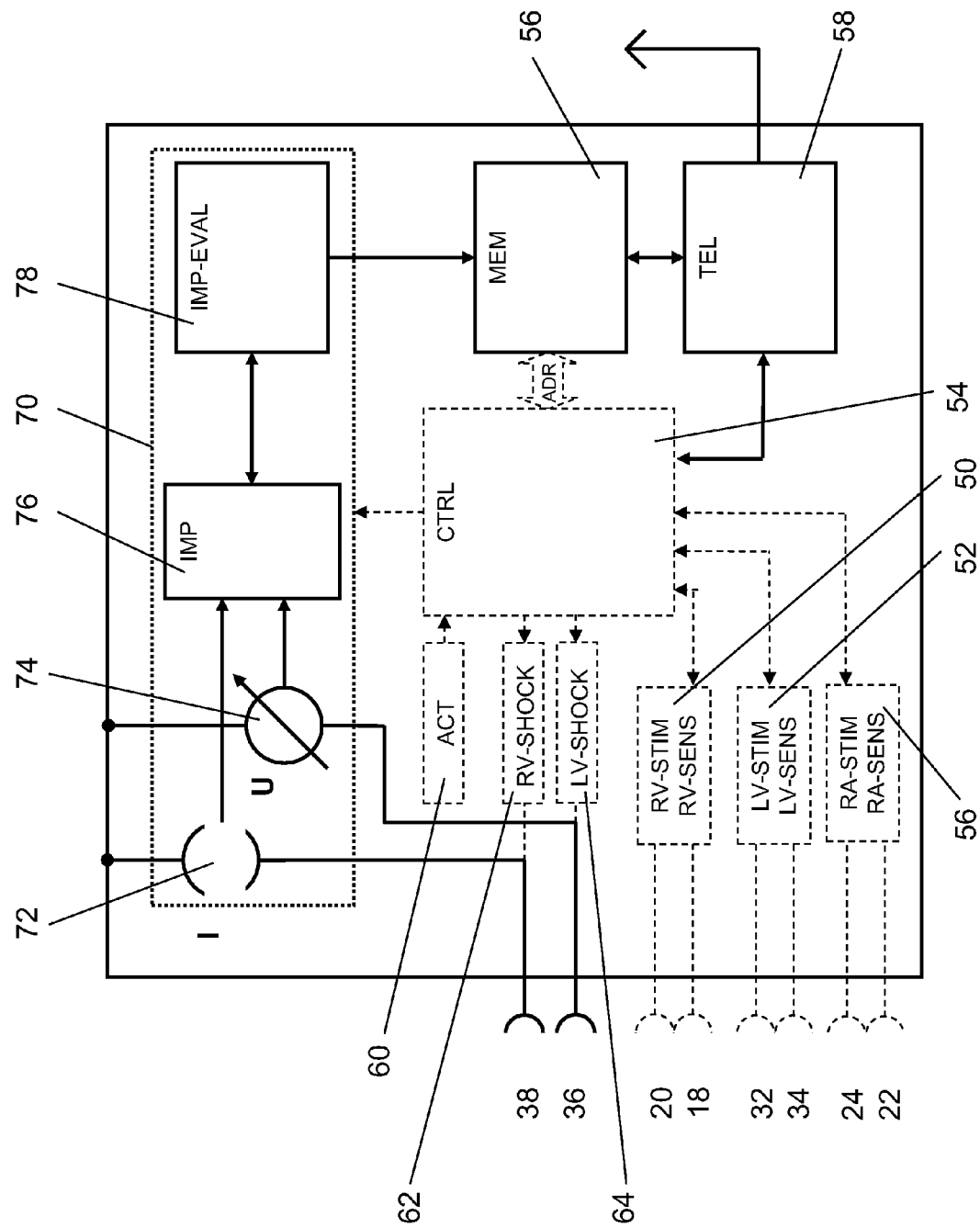
FIG. 3 is a schematic diagram of the device modules of the ICD of FIG. 3.

Referring to FIG. 3 a simplified block diagram of an implantable medical device 10 is illustrated. During operation of the pacemaker leads 14 and 16 are connected to respective output/input terminals of pacemaker 10 as indicated in FIG. 2 and carry stimulating pulses to the tip electrodes 18 and 22 from an right atrial stimulation pulse generator RA-STIM in a right atrial sense/pace stage 56 and a right ventricular pulse generator RV-STIM in a right ventricular sense/pace stage 50, respectively. Further, electrical signals from the atrium are carried from the electrode pair 18 and 20, through the lead 14, to the input terminal of an right atrial channel sensing stage RA-SENS in 56; and electrical signals from the right ventricle are carried from the electrode pair 22 and 24, through the lead 16, to the input terminal of a right ventricular sensing stage RV-SENS in 50.

Left ventricular stimulating pulses are carried to the ring electrode 32 and the tip electrode 34 from a left ventricular pulse generator LV-STIM in the left ventricular sense/pace stage 52. Electrical signals from the left ventricle are carried from the electrode pair 32 and 34 to the input terminal of the left ventricular sensing stage RV-SENS in 52.

Controlling the implantable medical device 10 is a control unit CTRL 54 that is connected to sensing stages A-SENS and V-SENS and to stimulation pulse generators A-STIM and V-STIM. Control unit CTRL 54 receives the output signals from the atrial sensing stage A-SENS and from the ventricular sensing stage V-SENS. The output signals of sensing stages A-SENS and V-SENS are generated each time that a P-wave representing an intrinsic atrial event or an R-wave representing an intrinsic ventricular event, respectively, is sensed within the heart 12. An As-signal is generated, when the atrial sensing stage A-SENS detects a P-wave and a Vs-signal is generated, when the ventricular sensing stage V-SENS detects an R-wave.

From a sequence of sensed R-waves control unit 54 can determine an intrinsic heart rate that is used for decompensation detection.

Control unit CTRL 54 also generates trigger signals that are sent to the atrial stimulation pulse generator A-STIM and the ventricular stimulation pulse generator V-STIM, respectively. These trigger signals are generated each time that a stimulation pulse is to be generated by the respective pulse generator A-STIM or V-STIM. The atrial trigger signal is referred to simply as the "A-pulse", and the ventricular trigger signal is referred to as the "V-pulse". During the time that either an atrial stimulation pulse or ventricular stimulation pulse is being delivered to the heart, the corresponding sensing stage, A-SENS and/or V-SENS, is typically disabled by way of a blanking signal presented to these amplifiers from the control unit CTRL 54, respectively. This blanking action prevents the sensing stages A-SENS and V-SENS from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called post ventricular atrial refractory period (PVARP) are generally recorded as atrial refractory sense event Ars but ignored.

Control unit CTRL 54 comprises circuitry for timing ventricular and/or atrial stimulation pulses according to an adequate stimulation rate that can be adapted to a patient's hemodynamic need as pointed out below.

Still referring to FIG. 3, the implantable medical device 10 includes a memory circuit MEM 56 that is coupled to the control unit CTRL 54 over a suitable data/address bus ADR. This memory circuit MEM 56 allows certain control parameters, used by the control unit CTRL 54 in control-ling the operation of the implantable medical device 10, to be programmable stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 56 for later retrieval and analysis.

A telemetry circuit TEL 58 is further included in the implantable medical device 10. This telemetry circuit TEL 58 is connected to the control unit CTRL 54 by way of a suitable command/data bus. Telemetry circuit TEL 58 allows for wireless data exchange between the implantable medical device 10 and some remote programming or analyzing device which can be part of a centralized service center serving multiple pacemakers.

The implantable medical device 10 in FIG. 3 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE, the atrial stimulation pulse generator A-STIM and corresponding portions of the control unit CTRL 54, are commonly referred to as the atrial channel. Similarly, those portions of the pacemaker 10 that interface with the right ventricle 28, e.g., the lead 16, the R-wave sensing stage V-SENSE, the ventricular stimulation pulse generator V-STIM, and corresponding portions of the control unit CTRL 54, are commonly referred to as the ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 54 of the pacemaker 10. While this sensor ACT 60 is illustrated in FIG. 2 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient. The output of sensor 48 represents an activity level.

By means of the output signal of activity sensor 60 the control unit 54 is able to assign each intrinsic heart rate to an activity thus enabling collection of intrinsic heart rate value for a patient's state of rest and a patient's state of exercise separately.

The control unit CTRL 54 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporeal placement as shown in FIG. 2. In order to allow for a plurality of impedance measurement electrode configurations, preferably some means of switching is provided between the constant current source 72 and the electrode terminals of the implantable medical device 10. The switch is not shown in FIG. 3. Rather, particular impedance measurement configurations are shown as examples.

Similarly, a impedance measuring unit 74 for measuring a voltage corresponding to a current fed through a body by said constant current source is provided and can be connected to a number of electrodes although a switch for switching between these configurations is not shown in FIG. 3.

As an alternative to constant current source 72 a constant voltage source can be provided to generate the forcing function. Then, the measuring unit will be adapted to measure a current strength of a current fed through a body by said constant voltage source.

Both, constant current source 72 and impedance measurement unit 74, are connected to an impedance value determination unit 76 that is adapted to determine an impedance value for each measuring current pulse delivered by the constant current source 72.

Further, an impedance measuring control and evaluation unit 78 is provided, that is connected to said impedance measurement unit and that is adapted to evaluate a sequence of consecutive impedance values determined by said impedance measurement unit. Impedance measuring control and evaluation unit 78 comprises a signal generator module (not shown) to construct the intra-cardiac impedance or conductance signal reflecting the time course of the impedance measurement unit's output signal and its derivative.

Impedance measuring control and evaluation unit 78 further comprises a filter module (not shown) to filter the intra-cardiac impedance signal. Impedance measuring control and evaluation unit 78 comprises is connected to memory 56 and to telemetry unit 58 to allow for storing of impedance data and further evaluation by an external service center.

Via intracardiac impedance measurement, control unit 54 is able to determine a stroke volume. From the stroke volume and the intrinsic heart rate the control unit calculates the cardiac output by multiplying the stroke volume and the heart rate.

Via intrathoracic impedance measurement control unit 54 is able to determine a tidal volume and a ventilation rate (breathing rate) in a manner generally known to the skilled person.

Thus, the control unit 54 collects data representing:
DC thoracic impedance from said first electrode combination
DC thoracic impedance from said second electrode combination
cardiac output
heart rate variability
heart rate at a resting state of a patient
heart rate during exercise of a patient
activity level of a patient
ventricular extra systoles (VES) per time unit
breathing rate
tidal volume once a day and initiates transmission of these data via the external transceiver to the central service center 90.

Figure 4:
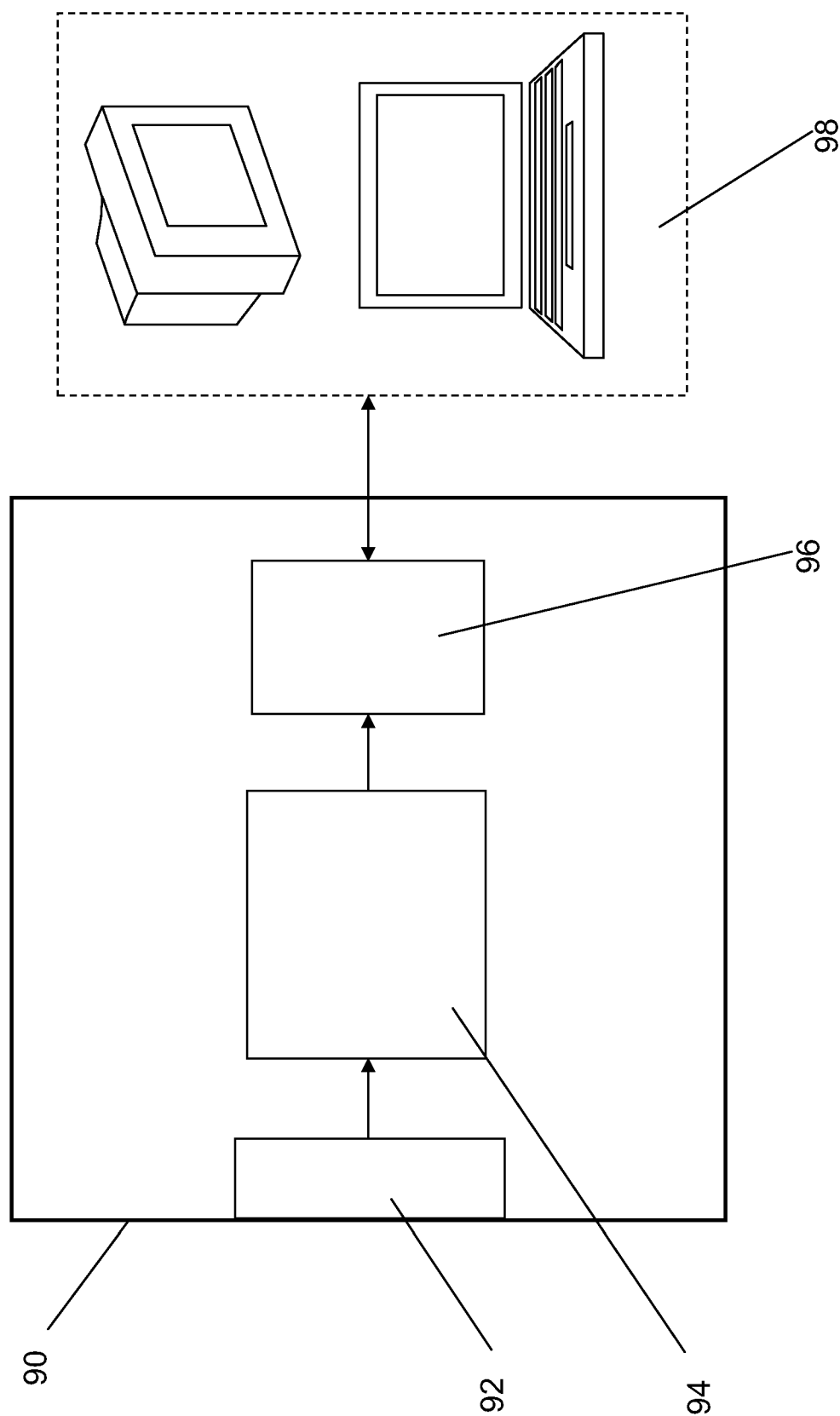
FIG. 4 is a schematic diagram of the service center.

FIG. 4 shows the central service center 90 comprising a data communication interface 92 for communicating with the external transceiver device 80. Connected to the data communication interface 92 is a central data base 94 for storing data representing measurements performed by the implantable medical device 10 and the external transceiver device 80. The central data base 94 is connected to a data evaluation module 96 that is adapted to evaluate data stored in said data base. The evaluation includes data trending of stored data.

Connected to the data analysis module is a user interface 98 for displaying data generated by the data analysis module 96 to a user allowing a user to enter instructions or data for controlling the data analysis module 96.

In addition to the data collected by the implantable medical device 10, the central service center receives data relating to
weight
blood pressure
parameter from at least another sensor (contractility, pressure, temperature) and
diet of a patient wearing the implantable medical device 10.

By the service center, the data is trended in one graph or more graphs to visually inspect trends and the timely coincidence of trends. The user interface 98 is adapted to allow the physician to set for each trend its own, patients customized trigger criteria. The trigger criteria may include offset versus baseline or slope (positive and negative) or others.

Preferably, the user interface 98 is adapted so that the physician can set trigger combination and its timely coincidence to receive an alarm triggered by the data evaluation module 96 when the trigger criteria are met and the data evaluation module generates a decompensation indicator signal. Then the service center 90 generates a decompensation alarm message that is transmitted to a physician via e-mail or otherwise. E.g. only by increase of both impedance vectors by x % and decrease of activity level by y % and increase of breathing rate by z % the service center triggers a decompensation alarm: "alarm—potential decompensation".

The service center and the user interface are adapted to interact such that
the user receives a set of standard triggers/trigger combination by the service center that is stored in the service center
the user can store its own trigger logic and apply it to other patients
a supervisor can collect the data of trigger logic from all patients and all users (physicians) and generated there from an improved set standard trigger criteria
Additional features of the system are:
Additional data is collected from outside sensors
Weight is determined via a scale which sends weight data to the service center
blood pressure data is send to the service center
Diet information data is determined via barcode in a refrigerator and is send to the service center
Duration of daily exercise (treadmill reports duration/speed/activity level) are transmitted to the service center
The data evaluation module trends the data with one datapoint per day for each trend.
The data evaluation module and the user interface and their interaction are adapted to allow a user to be able to activate/deactivate trigger for each trend (absolute value, positive/negative slope, duration of increase, 30 day line (to compensate for biological variations), 7 day line)

a user to be able to combine trigger to trigger logic comprising a combination of trigger criteria to be met a definition of a timely coincidence of triggers ("within 2 days")

The data evaluation module and the user interface are further adapted to generate a display of data wherein graph-lines changes colors for each trend separately if trigger is not reached ("green") versus trigger is reached ("red")

a display of data wherein a graph background changes colors for times for which the trigger logic was giving alarm ("alarm background")

Once a potential decompensation is detected the service center 90 indicates a decompensation via the user interface 98 and allows the physician to initiate therapy changes actively via several remote activities including:

Change of CRT parameters (e.g. % LV pacing was seen to be insufficient, then AVD would be adapted) via remote programming via the user interface Change of diet via telephone call to the patients Change of medication (e.g. Lasix) via telephone call to the patients Change of medication (e.g. Lasix) via remote programming of a drug pump using the user interface of the service center.

Further, a feedback channel (not shown) from an individual patient to the physician is provided that allows for a feedback whether a therapy change was successful or not.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of heart monitoring systems by following the present teachings. All such changes, modifications and alterations should therefore be recognized as falling within the scope of the present invention.

What is claimed is:

1. A heart monitoring system comprising:
    an implantable medical device;
    a service center;
    a central data base;
    a user interface;
    said implantable medical device comprising
        a stimulation pulse generator configured to generate electric stimulation pulses and configured to connect to at least a ventricular stimulation electrode configured to deliver said electric stimulation pulses to at least a ventricle of a heart;
        a ventricular sensing stage configured to connect to an electrode configured to pick up electric potentials inside said at least said ventricle of said heart, said sensing stage configured to sense an excitation or a contraction of ventricular myocardium;
        an activity sensor;
        an impedance determination unit comprising
            a constant current source or a constant voltage source having current feed terminals that are configured to connect to electrodes for intracorporeal placement wherein said constant current source or said constant voltage source is configured to generate sub-threshold measuring current pulses having a constant current strength or a constant voltage, respectively, that cause a current to be fed through a body via intracorporeally placed electrodes;
            a measuring unit configured to measure a voltage corresponding to said current fed through said body by said constant current source or a current strength of said current fed through said body by said constant voltage source, respectively;
            an impedance value determination unit that is connected to said constant current source or said constant voltage source wherein said measuring unit is configured to determine an impedance value for each of said sub-threshold measuring current pulses;
            said impedance determination unit configured to perform an intrathoracic impedance measurement via a first and a second electrode combination wherein said second electrode combination is different from said first electrode combination;
        a battery;
        a control unit that is connected to said battery, said stimulation pulse generator, said ventricular sensing stage, said activity sensor and said impedance determination unit and that is configured to collect data representing values of:
            DC thoracic impedance from said first electrode combination,
            DC thoracic impedance from said second electrode combination,
            cardiac output,
            heart rate at a resting state of a patient,
            heart rate during exercise of said patient,
            activity level of said patient,
            ventricular extra systoles or VES per time unit,
            breathing rate,
            tidal volume;
        an implant transceiver unit configured to communicate with said service center;
    said service center comprising another data communication interface configured to allow at least an indirect data communication with said implantable medical device wherein said another data communication interface is connected to said central data base and to said user interface;
    wherein said control unit is configured to initiate transmission of said collected data to said service center;
    said service center further comprising a data evaluation module connected to said data base wherein said data evaluation module is configured to evaluate data stored in said data base including data trending of stored data, wherein said data evaluation module is further configured to generate a decompensation indicator signal if a change in said DC thoracic impedance from said first electrode combination and said DC thoracic impedance from said second electrode combination show a preset increase and activity level shows a preset decrease and said breathing rate shows a second preset increase; and,
    said user interface and said data evaluation module are further configured to allow a physician to set for each data, trend trigger criteria that signifies detection of decompensation and wherein said data evaluation module is further configured to generate said decompensation indicator signal whenever a combination of trigger criteria are met by trended data.

2. The heart monitoring system according to claim 1, wherein said heart monitoring system further comprises an external transceiver device and wherein said external transceiver device comprises an external transceiver unit for wireless communication with said implant transceiver unit and a data communication interface configured to allow a data communication with said service center.

3. The heart monitoring system according to claim 1, wherein said trigger criteria includes an offset versus baseline or slope of said trended data as to trigger generation of said decompensation indicator signal whenever said offset is exceeded.

4. The heart monitoring system according to claim 1, wherein said data evaluation module is configured to generate said decompensation indicator signal whenever a plurality of trigger criteria are met in a preset timely coincidence.

5. The heart monitoring system according to claim 1, wherein user interface is configured so that a user can set
 trigger combinations or timely coincidence of trends or
 trigger combinations and timely coincidence of trends.

6. The heart monitoring system according to claim 1, wherein said service center is to transmit a decompensation alarm message whenever said data evaluation module generates said decompensation indicator signal.

7. The heart monitoring system according to claim 1, wherein said implantable medical device is configured to transmit collected raw data daily to said service center.

8. The heart monitoring system according to claim 1, wherein said data evaluation module is configured to trend said data with one datapoint per day for each trend.

9. The heart monitoring system according to claim 1, wherein said data evaluation module and said user interface and their interaction are configured to allow a user to be able to activate or deactivate triggers for each trend.

10. The heart monitoring system according to claim 1, wherein said data evaluation module and said user interface and their interaction are configured to allow a user to be able to combine triggers to trigger logic comprising a combination of trigger criteria to be met.

11. The heart monitoring system according to claim 1, wherein said data evaluation module and said user interface and their interaction are configured to generate a display of data having graph-lines wherein said graph-lines change color for each trend separately if a trigger is not reached versus if said trigger is reached.

12. The heart monitoring system according to claim 1, wherein said data evaluation module and said user interface and their interaction are configured to generate a display of data having a graph background wherein said graph background changes colors for times for which trigger logic produces an alarm.

13. The heart monitoring system according to claim 1, wherein said service center is configured to indicate a decompensation alarm via said user interface connected to said service center and to allow the physician to initiate therapy changes actively via several remote activities including:
 change of pacing parameters via remote programming via the user interface;
 change of diet via telephone call to said patient;
 change of medication via telephone call to said patient; and,
 change of medication via remote programming of a drug pump via the user interface of the service center.

14. The heart monitoring system according to claim 1, further including a feedback channel from an individual patient to said user interface that allows for feedback to indicate whether a therapy change was successful or not.

* * * * *